United States Patent [19]
Akers et al.

[11] Patent Number: 6,112,182
[45] Date of Patent: *Aug. 29, 2000

[54] METHOD AND APPARATUS FOR INTEGRATED MANAGEMENT OF PHARMACEUTICAL AND HEALTHCARE SERVICES

[75] Inventors: William Rex Akers, Colleyville; Michael Wayne Paris, Mansifield; Teresa A. Strickland, Springtown; Deborah L. Jenkins Kilburn, Fort Worth, all of Tex.

[73] Assignee: Healthcare Computer Corporation, Fort Worth, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/585,861

[22] Filed: Jan. 16, 1996

[51] Int. Cl.[7] ...................................................... G06F 17/60

[52] U.S. Cl. .................................... 705/2; 705/3; 707/104

[58] Field of Search ................................ 364/400; 705/2, 705/3, 4; 707/100, 104; 700/90

[56] References Cited

U.S. PATENT DOCUMENTS

| | | | |
|---|---|---|---|
| 4,723,212 | 2/1988 | Mindrum et al. | 705/14 |
| 4,910,672 | 3/1990 | Off et al. | 705/14 |
| 5,173,851 | 12/1992 | Off et al. | 705/14 |
| 5,519,607 | 5/1996 | Tawil | 705/2 |
| 5,550,734 | 8/1996 | Tarter et al. | 705/2 |
| 5,660,176 | 8/1997 | Iliff | 128/630 |
| 5,666,492 | 9/1997 | Daniel et al. | 705/3 |
| 5,737,539 | 4/1998 | Edelson et al. | 705/3 |
| 5,758,095 | 5/1998 | Albaum et al. | 705/2 |

OTHER PUBLICATIONS

Healthcare Computer Corp., 1995, ALPHA–PC™ User Manual, pp. 1–1 to 14–16 GL–1 to GL–20.

*Primary Examiner*—Edward R. Cosimano
*Attorney, Agent, or Firm*—Carr & Storm, L.L.P.

[57] ABSTRACT

A computer-based pharmaceutical practice management system and a healthcare management system for use by a pharmacy includes a processes by which health conditions of a patient, drugs taken the patient and other information gathered by the pharmacist with the practice management system in connection with dispensing the will automatically initiate related actions handled by processes of the healthcare management system.

20 Claims, 13 Drawing Sheets

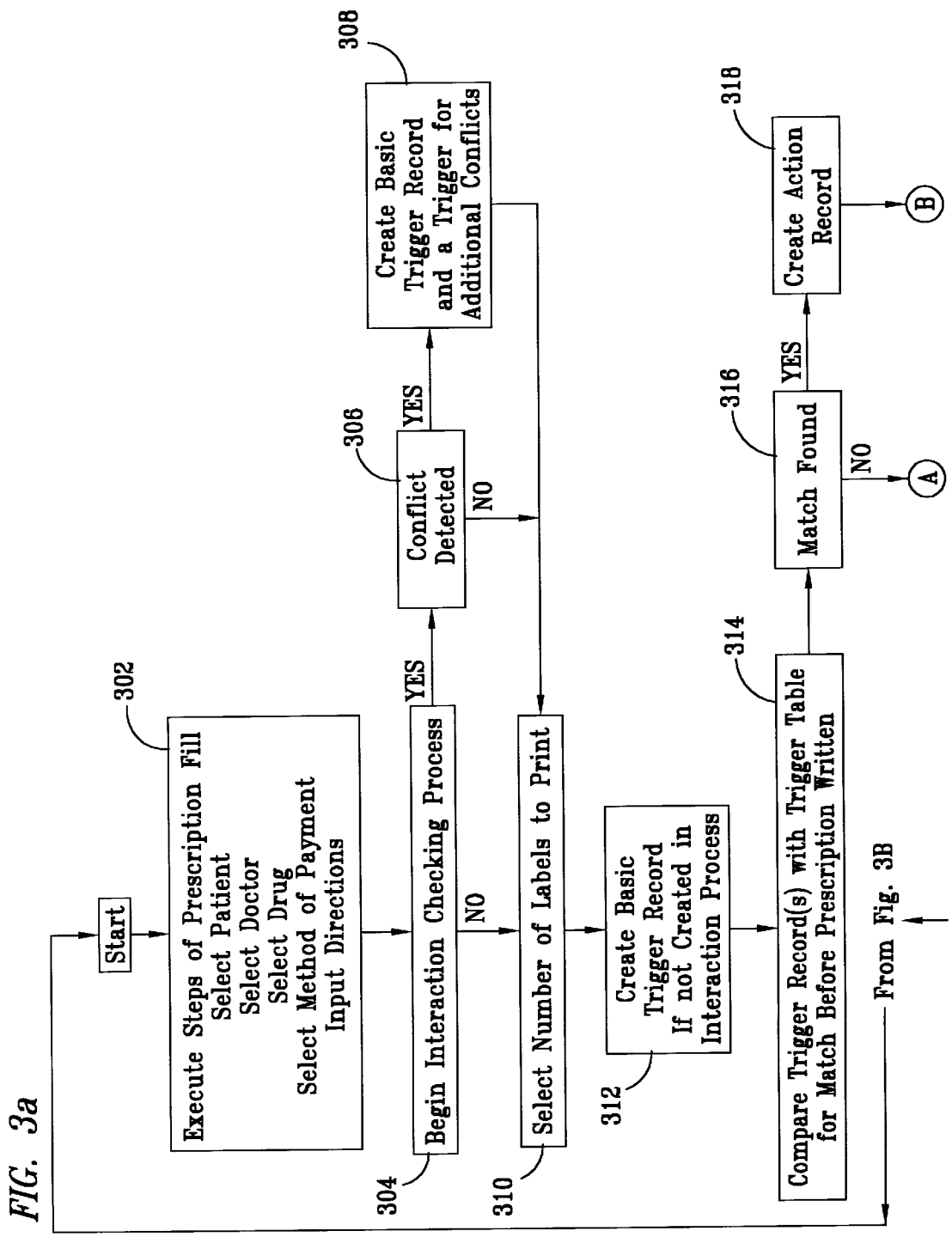

FIG. 5b

```
Rx800                  PC040: Patient Care Action Edit / Version 4.2
           12/27/95      Patient Care Recommendations      19:02:21
** Patie   Patient Name FLEMING, DANIEL                              800 422
   Addre   Rx/Refill           -00 Ref#   10    Date 12/27/95        99999.00
   PP A                                                                626.15
** Docto                                                               300.00
   # 39    Ln Status  Protocol                    Action     Fee      Current
** Drug                                                              07/12/95
           1.    Y    Schedule for Weekly Monito Appointmen  5.00
** Plan    2.    Y    Hypertension Diet Instruct             2.00    PS   3  D
   Pqty                    ╲
   Dqty                     523         ╲                            Orgrf    2
   5.19                                  522
   Retai
   Sigs                                                              12/27/96
                                                                     12/27/96

┌─────────────────────────────────┐
                              │ 1. Initiate All    3. Print List│
                              │ 2. Change Status   X. Exit Menu │╲
                              │         Selection = ☐           │ 524
                              └─────────────────────────────────┘

Rph D      <F2> Abort   <F5> Help   <F6> Calc    <F8> PrtScr    Prf
<F1> B
```

FIG. 5c

```
┌─────────────────────────────────────────────────────────────────────┐
│ Rx800         PC040: Patient Care Action Edit / Version %I%  800 422│
│ 12/27/95         Patient Care Recommendations      19:02:21         │
│ **Patie Patient Name FLEMING, DANIEL                                │
│   Addre                                                   99999.00  │
│   PP A   Rx/Refill       -00 Ref#    10    Date 12/27/95    626.15  │
│ **Docto                                                     300.00  │
│   #39                                                               │
│ **Drug   Ln Status Protocol                 Action   Fee   Current  │
│                                                            07/12/95 │
│   Plan   1.   [Y]     Schedule for Weekly Monito Appointmen  5.00   │
│   Pqty   2.    Y      Hypertension Diet Instruct             2.00   │
│   Dqty        ↑                                                     │
│  [5.19]      523              ↑                           PS  3  D  │
│   Retai                      522                                    │
│   Sigs                                                    Orgrf  2  │
│                         ┌─ Status Codes & Meanings ─┐               │
│                         │ Y:  Initiate Action When Instructed to    │
│                         │ I:  Initiate This Action Immediately      │
│                         │ N:  Do Not Initiate This Action (Skip)    │
│                         │ D:  This Action Line Has Been Closed      │
│                         └───────────────────────────┘               │
│                                    ↑                      12/27/96  │
│                                   526                     12/27/96  │
│ Rph D                                                               │
│ <F1> B  <F2> Abort  <F5> Help  <F6> Calc  <F8> PrtScr        Prf    │
└─────────────────────────────────────────────────────────────────────┘
       ↑
      520
```

FIG. 5d

```
Wednesday 12/27/95 ─── PC300: Patient Scheduling Screen / Version 4.20 ───
Line  Time  Tch   Patient        P r o c e d u r e s                          Phone #    St
              ─── PC215: Patient Appointment Screen / Version 4.21 ───
   Patient        FLEMING, DANIEL                    Phone  817-455-2875
   Address        3100 BROOKSHIRE                    Date of Birth  01/05/48
   Address2
   City/St/Zip    FT. WORTH          TX 76103

RPh/Tech              DBF  DAVID FREEMAN
   Appointment Date      01/04/96             16:00         Thursday
   Monitoring        1.  BP                2.          3.
   Procedures        4.                    5.
   Status (S/R/C/X/N/D)  S Scheduled
   Freq (D/W/S/M/Q/A)    W Weekly
   Next Appointment      01/11/96             16:00         Thursday
   Comment               Patient May Need To Be Reminded By Phone All ok?  (Y/N)   Y <F1> Bottom   <F2> Abort   <F5> Help   <F6> Calc   <F8> PrtScr
```

```
┌─────────────────────────────────────────────────────────────────────────┐
│         PC210: Patient Services / Version %I%                           │
│                                         A/R Acct                        │
│  Patient   DOE, JOHN JR                 A/R Max   99999.99   Bal Current│
│  Address   1234 MAIN ST                           CurBal          .00   │
│       ─── PC215: Patient Appointment Screen / Version %I% ───           │
│                                                                         │
│  C  Patient         DOE, JOHN JR              Phone  817-444-4444       │
│  P  Address         1234 MAIN ST                                        │
│  D  Address2                                  Date of Birth  01/01/82   │
│  R  City/St/Zip     FT. WORTH       TX 777777                           │
│                                                                         │
│     RPh/Tech               TL     TIM LESLIE                            │
│     Appointment Date       01/12/96   Friday     Time    11:00          │
│     Monitoring         1.  BP              2.            3.   Length 15 │
│     Procedures         4.                  5.                        3. │
│     Status (S/R/C/X/N/D)   S  Scheduled                                 │
│     Freq (D/W/S/M/Q/A)     W  Weekly                                    │
│     Next Appointment       01/19/96   Friday     Time    11:00       3. │
│     Comment                                                             │
│                                                                         │
│                            All ok?  (Y/N)   Y                           │
│                                                                         │
│  ┌────────┐ ┌────────┐ ┌────────┐ ┌────────┐ ┌────────┐                 │
│  │<F1>    │ │<F2>    │ │<F5>    │ │<F6>    │ │<F8>    │                 │
│  │ Bottom │ │ Abort  │ │ Help   │ │ Calc   │ │ PrtScr │                 │
│  └────────┘ └────────┘ └────────┘ └────────┘ └────────┘                 │
└─────────────────────────────────────────────────────────────────────────┘
```

FIG. 7b

```
—— PC840: Patient Care Action Edit / Version %I% ——
01/12/96        Patient Care Recommendations
Patient Name  DOE, JOHN JR
Rx/Refill              -00  Ref#  1696        Date 01/12/96

Ln Status  Protocol                                    Action    Fee
1.   Y     Hand Out Worksheet #1
2.   Y     Schedule Next Appointment
3.   Y     Check and Record Blood Pressure and Pulse 1. Initiate All        3. Print List
    2. Change Status       X. Exit Menu Selection = ☐

<F2> Abort    <F5> Help    <F6> Calc    <F8> PrtScr
```

Patient
Address

C  Patie
P  Addre
D  Addre
R  City/
   RPh/T
   Appoi
   Moni
   Proc
   Statu
   Freq
   Next
   Comme Current  .00

15

METHOD AND APPARATUS FOR INTEGRATED MANAGEMENT OF PHARMACEUTICAL AND HEALTHCARE SERVICES

FIELD OF THE INVENTION

The invention pertains generally to data processing systems and more particularly to data processing systems used to manage delivery of healthcare services.

BACKGROUND OF THE INVENTION

A current trend in medical care is the increasing use of healthcare-related services which are rendered outside the direct supervision of a doctor. Such services may relate directly to a disease, illness or other medical condition of the patient, to drugs or other therapies prescribed for the patient, or to lifestyle or behavior changes intended to benefit the health of the patient. Such services are numerous and diverse. Briefly, examples of such services include developing and implementing therapeutic protocols, implementing strategies to utilize drug therapies, and monitoring health, lifestyle and disease states and conditions, all with the goal of efficiently and effectively enhancing or improving a patient's quality of life and effectively managing healthcare costs. A variety of computer programs have been used for developing protocols, programs and strategies, and monitoring progress in connection with delivery of these services.

Doctors may recommend to their patients to seek out these services. However, doctors may be unaware or not financially motivated or sufficiently interested in providing or recommending the services. Furthermore, doctors are often not in a position to follow up with a patient to ensure that the patient has sought these services, especially when the patient does not see the doctor on a frequent basis. Due to a lack of medical or other professional health training, a patient may be unaware of such services. The patient may also be unable to identify appropriate services, or feel comfortable that he or she has selected an appropriate service. Thus, a patient may often not timely receive the benefit of appropriate supplemental healthcare services.

SUMMARY OF THE INVENTION

To better enable patients to utilize supplemental healthcare services which are not necessarily rendered under the immediate supervision of a doctor, the invention provides for a computer-based apparatus and process by which a care service or other healthcare related action appropriate for a particular individual or patient is identified, initiated and/or provided through use of a second data process.

According to one aspect of the invention, a computer based process used to manage dispensing of drugs at a pharmacy triggers a pharmacist or other user to take a further patient care action managed by a second computer process in response to predefined data items used in connection with the transaction. During such a process, data for the patient, doctor, drug, and disease states for the patient, for example, will be recorded or used during the transaction. A user-defined, preprogrammed trigger associated with one or more data items used in connection with a prescription dispensing transaction causes at least one patient care action to be listed in a queue for subsequent review and/or action based on patient's health state. The action is used to initiate a process for managing a care service process provided by a pharmacist or technician. For example, such care process could include scheduling an appointment for monitoring lifestyle, health or disease states or conditions, printing information on the dispensed drug, initiating a lifestyle monitoring process designed to improve the health of the patient, recording an intervention, performing patient counselling and performing a subjective, objective, assessment and planning (S.O.A.P.) protocol in connection with drug therapies. Care processes may also include, for example, printing a claim form or submitting a claim to an insurance company, printing coupons or other information for complementary or alternative drugs and issuing a rebate for the drug.

The advantages of such an apparatus and process are that appropriate patient healthcare services may be automatically identified during dispensing of a pharmaceutical. The pharmaceutical drugs are often prescribed by a doctor. In many cases, a pharmacist will have kept a database of information of current medications and diseases and states of the patient being treated by the drugs. Thus, the appropriateness of the indicated healthcare service is more greatly assured. In many cases, the patient will typically have at least one contact with the pharmacist, and often more frequent contact than with other healthcare related providers. Consequently, a patient is more likely to receive appropriate information about and delivery of these healthcare services.

According to other aspects of the invention, information provided by a patient concerning the patient's lifestyle and health history may be used in combination with information about the patient gathered or recorded in connection with dispensing pharmaceutical drugs in order to initiate a healthcare related service appropriate for the patient.

These and other aspects and advantages of the invention are illustrated by an embodiment described below in reference to the accompanying drawings.

BRIEF DESCRIPTION OF DRAWINGS

FIGS. 3a and 3b is a flow diagram illustrating a linking process between a prescription processing function in a pharmacy practice management system and a patient care service process for automatically executing a patient care process.

FIGS. 5a–5d are representative screens displayed in connection with the process illustrated by FIGS. 3a and 3b.

FIGS. 7a–7b are representative screens displayed in connection with the process illustrated by FIGS. 6A–6C.

DESCRIPTION OF PREFERRED EMBODIMENT

Figure 1:
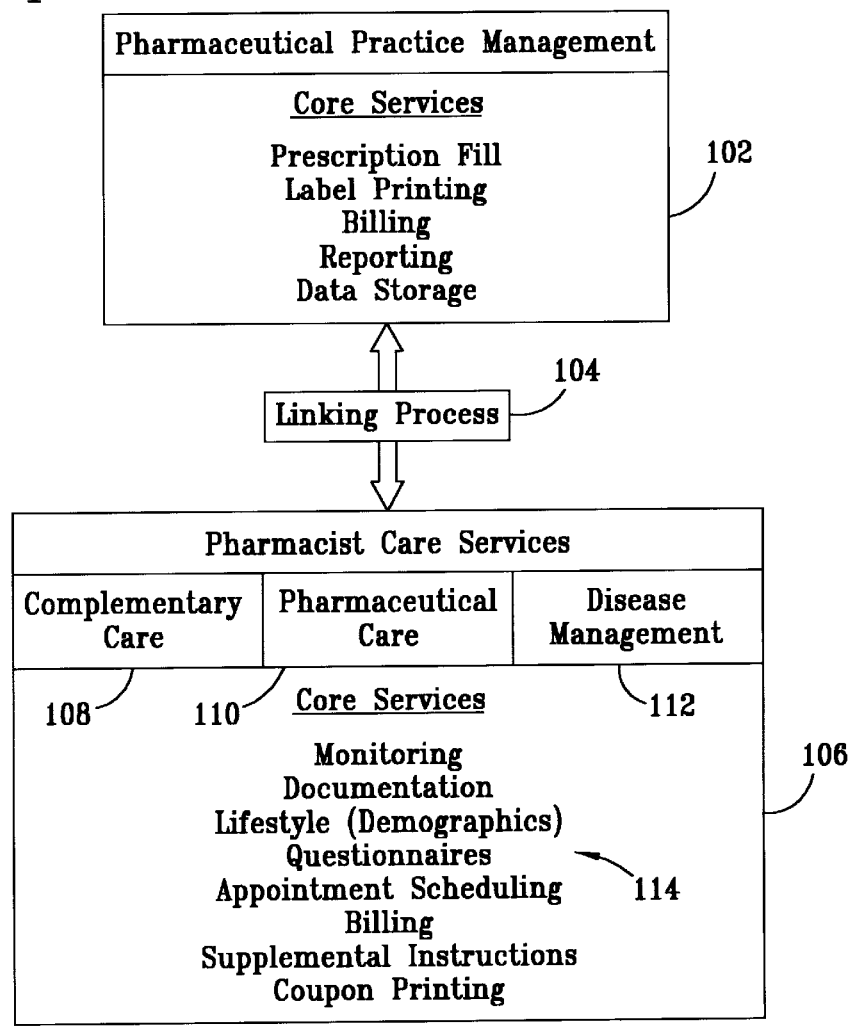
FIG. 1 is a schematic diagram of pharmacy practice management system, linking process, and pharmacy care management system for performing data processing functions according to the present invention.
Figure 2:
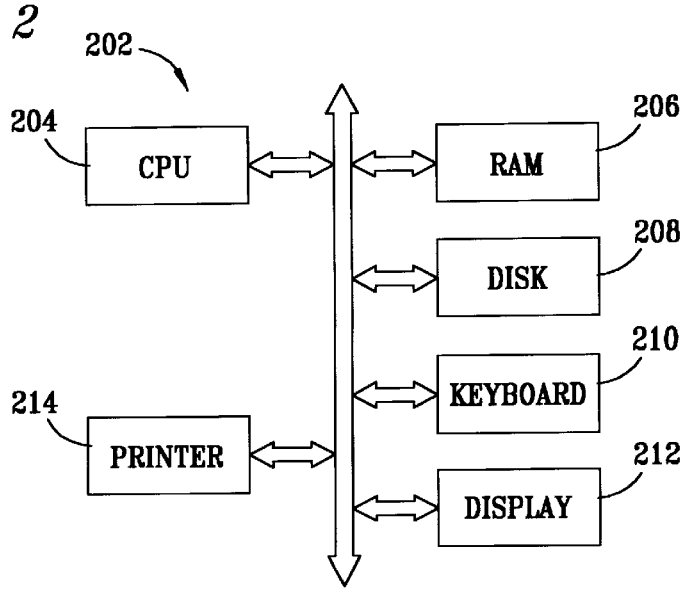
FIG. 2 is a schematic of a representative computer capable of being specially programmed to execute processes for the pharmacy practice management system, linking process, and a pharmacy care management system of FIG. 1.

FIG. 1 is a schematic representation of a pharmacy practice management process 102, a linking process 104 and a pharmacist care service management system 106. The system 102 and 106, and the linking process 104, are carried by a data processing system or machine such as a specially programmed computer 202 shown in FIG. 2. Computer 202 is typically located in a pharmacy, at or near a point of sale. It can take the form of any sort of computer, including an IBM compatible personal computer with a 486 or better microprocessor running DOS and 8 megabytes of random access memory (RAM). Typically, it includes a CPU 204 for executing instructions stored in program files; a working memory 206 such as RAM for use by the CPU in temporarily storing program and data files; a nonvolatile memory 208 such as a hard disk drive and/or removable magnetic disk drive for permanently storing data, text and program files; a keyboard 210 and/or other means for entering data; a video display 212 for visual information; and a printer 214. Additional input/output devices can be included for reading and storing files and for communication. No particular type hardware or software platform is required for carrying out the invention, so long as it is capable of executing the processes herein described. Alternately, in place of computer 202, the systems 102 and 106, and process 104 can be programmed for execution on network of computers, such as on a host or server computer which executes the programs and/or stores data files and communicates with client computers at or near the point of sale. Also, the processes can be integrated with processes used in recording point of sale transactions, inventory control, accounting and other functions for a pharmacy.

Referring back to FIG. 1, pharmacy practice management system 102 executes several known processes when running on computer 202. One example of a commercial pharmacy practice management system is software for running on an IBM standard computer sold under the trademark ALPHA-PC™ Practice Management System by Healthcare Computer Corporation of Fort Worth, Tex. This system is distributed as executable program files and linked libraries on magnetic media such as diskettes. A user loads this system onto computer 202, storing the files permanently on a hard disk in the computer. The programs, when executed by the computer, enable a pharmacist to store data gathered in connection with dispensing and selling pharmaceutical drugs. For example, data files can be maintained on prescriptions filled, patients, doctors, drugs, insurance plans. Core services or processes of such a practice management system include prescription filling, label printing, billing, reporting and data storage, including file maintenance, editing, and other housekeeping functions.

Pharmacist care processes 106 are used in connection with administration of healthcare services not rendered under the immediate supervision of a doctor, but which directly or indirectly benefit the health or quality of life of a patient. These processes include a program or collections of programs, or processes, for managing delivery of complementary care 108, pharmaceutical care 110, and disease management 112. These programs are also executed by software running computer 202. An example of commercially available software for system 106 is sold under the trademark ALPHA-CARE™ by Healthcare Computer Corporation of Fort Worth, Tex.

These care management services are generally known and thus will be only briefly described. The pharmaceutical care processes 110 facilitates implementation of strategies which attempt to utilize drug therapies more efficiently to improve a patient's quality of life and to effectively manage healthcare costs. For example, this would include patient counselling as mandated by statute and preparing notes or observations based on a subjective, objective, assessment planning protocol (S.O.A.P.). The disease management process 112 facilitates implementation of therapeutic protocols designed to improve a patient's health and well-being.

The complementary care process 108 enables defined healthcare related actions to be triggered under user-defined conditions during execution of a prescription filling process of practice management system 102, or by one of the processes in the pharmacist care services management system 106. This triggering is handled by linking process 104, which receives data from both of the systems. These actions may include, for example, scheduling appointments with healthcare providers for monitoring lifestyle, health and disease states, recording interventions or prompting recommendations. They also may include issuing or printing coupons for drugs or other items, printing drug information and printing supplemental instructions relating to use of the drug.

Additionally, the pharmacy care services management system 106 includes a set of core services or processes 114 which are shared by the complementary care, pharmaceutical care and disease management processes. These core services include, for example, appointment scheduling for patients and billing functions for care services. Such services further include maintaining records kept in connection with monitoring of patients, notes and lifestyle information on patients such as information on smoking, drinking, exercise, past illnesses, injuries and operations. Also, the services will function to print documentation, supplemental instructions and coupons, as well as generate questionnaires for use in gathering information from patients for use in connection with the other processes.

Figure 3B:
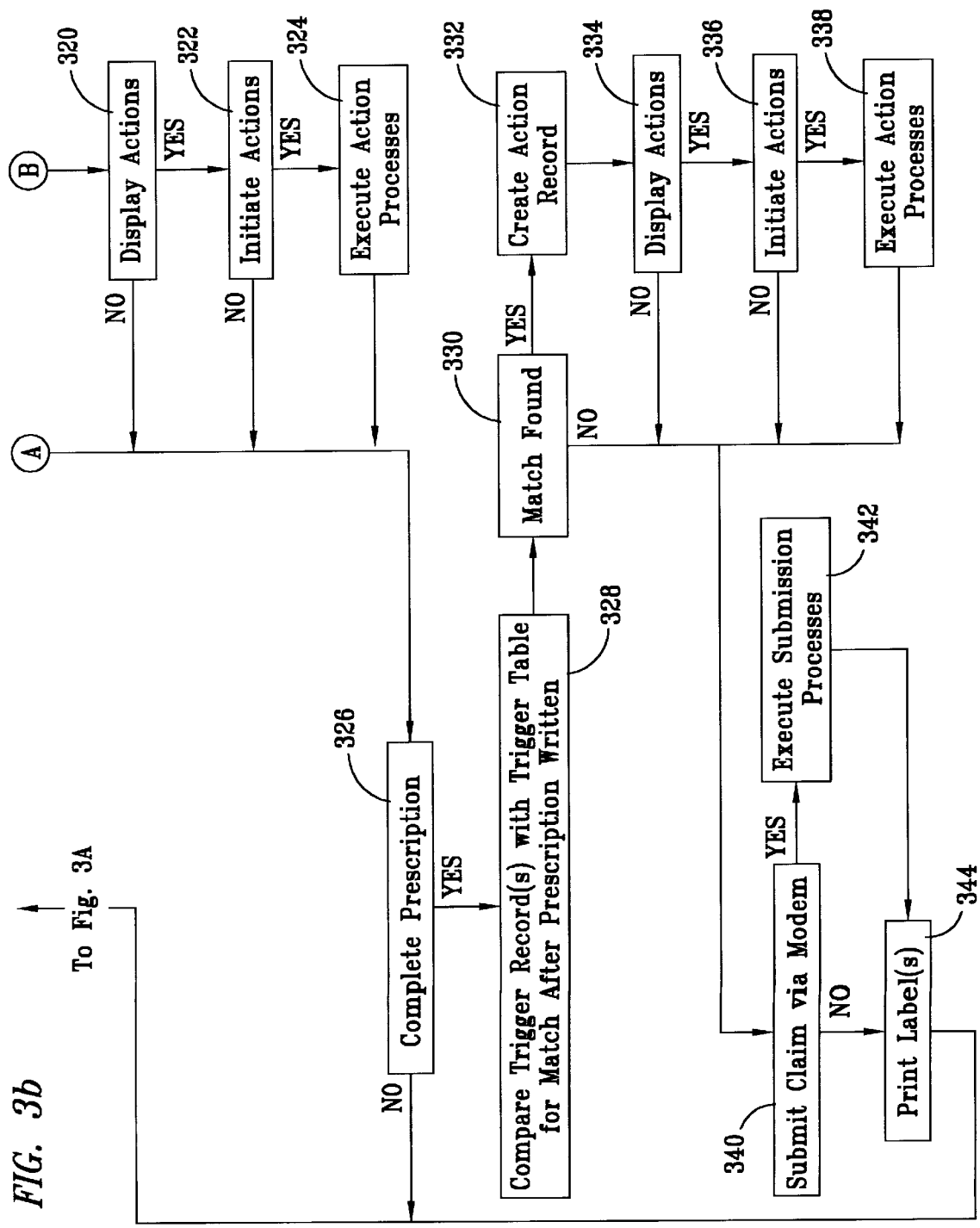
Figure 4:
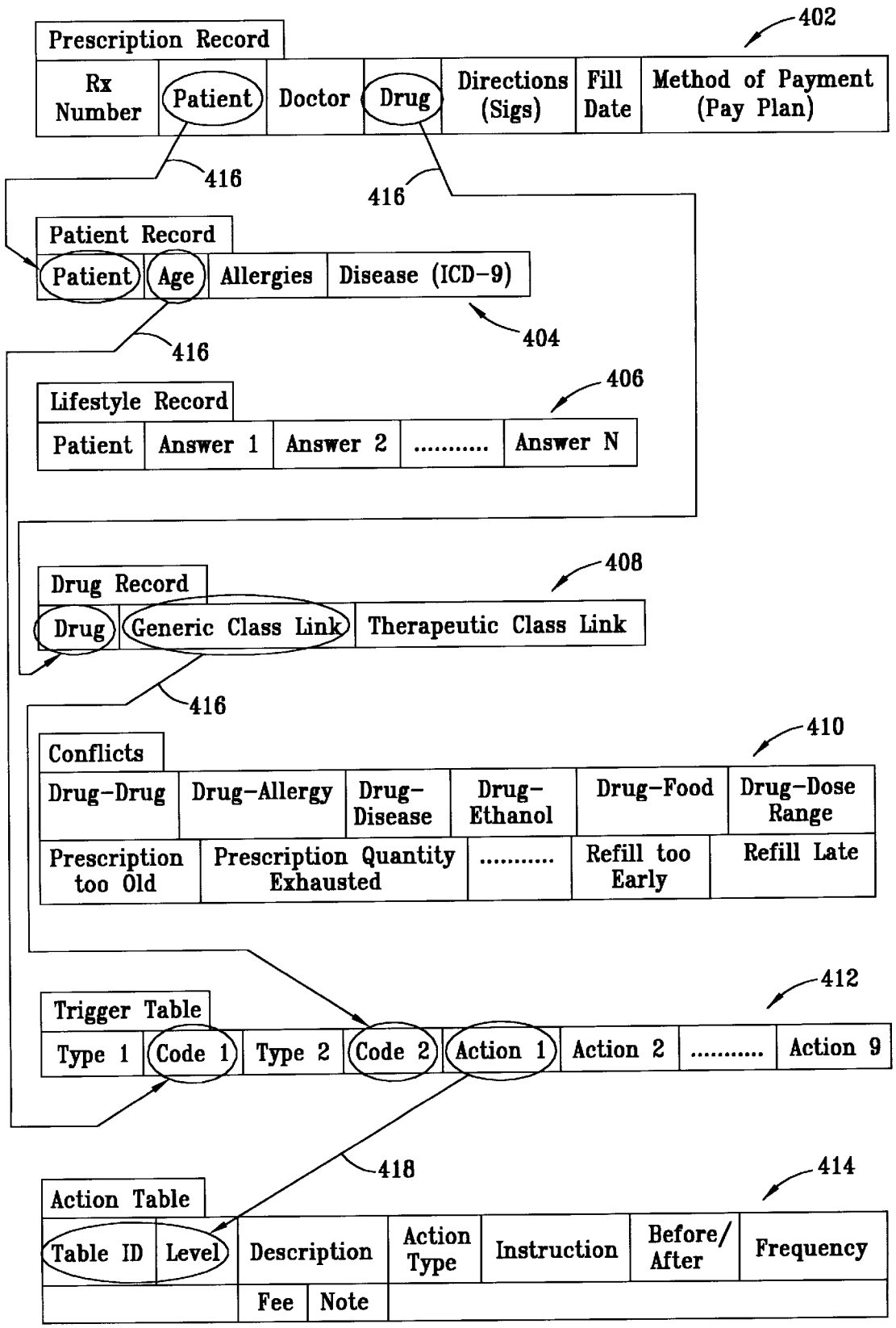
FIG. 4 represents the data structures of records and tables kept by a pharmacy practice management system for use in a linking process illustrated by FIG. 3.

Referring now to FIGS. 3a, 3b, and 4, the triggering or linking process 104 (FIG. 1) is illustrated in connection with refilling a prescription for a patient using the pharmacy management system 102 is running on computer 202. The process starts and, at step 302, requires the pharmacist to select a patient, doctor, a drug (identified by a NDC code), and method of payment. Separate tables are maintained in a database file(s) for storing data on the patients, the doctors, the drugs and the prescriptions. FIG. 4 illustrates the record structures for some of these tables which will be discussed in connection with the linking or triggering process. The pharmacist also enters, at step 302, directions for taking the drug. The patient, drug, doctor, payment plan, fill data and directions are stored as a new record in a prescription record table 402 once the prescription process is completed. This new record is assigned a prescription number.

Beginning at step 304, the practice management system begins a process of automatically checking for adverse interactions that the prescribed drug may have with other drugs previously dispensed to the patient or with alcohol and food, and for possible adverse reactions of the patient to the drug due to allergies to previously recorded conditions of the patient such as allergies. The drug conflict information is maintained in conflict table 410. Since this process is well known, it will not be described here.

If, as indicated by decision step 306, a conflict is detected, this conflict is displayed on the screen of the computer to the pharmacist. Additionally, at step 308, a trigger record for the transaction is created in which the data items (i.e. the type and code or, in other words, field and value) associated with the particular prescription filing transaction are recorded, as well as any data items associated with the conflict. This trigger record will be subsequently compared with trigger table 412 to determine whether or not any of the data elements associated with the particular prescription filling transaction are assigned triggers. For example, in the trigger record will be recorded the data items in the record for that patient found in table 404, the data items for the lifestyle record for that patient found in table 406, the data items for the drug found in drug record table 408, and the data item(s) in the conflict table 410 giving rise to the conflict. Additionally, although not illustrated, the name of the doctor is also included, as well as any data items found in a record for the particular doctor.

The patient records are self-explanatory. As shown by data record structure 404, each entry includes data items for name, age, allergies, disease states and other information such as address and telephone number (not shown). Lifestyle records, as represented by record structure 406, includes data for answers to questionnaires answered by the patient. Answers may include information on whether the patient drinks, smokes or is overweight, and past injuries, diseases and illnesses. Drug records, as represented by drug record structure 408, include the drug name or NDC code, generic class code, therapeutic class code and other information (not shown) such as manufacturer.

If no conflict is detected or found for the drug or prescription in the conflict table 410, or if there is no interaction process required (if it is an over the counter purchase, for example), the pharmacist enters the number of labels to print at step 310.

If a trigger record has not been created in step 308, one is created at step 312 using the basic prescription data elements for patient, doctor, drug, and patient lifestyle information. At step 314, the trigger record is compared to a trigger definition table 412 to determined whether there is a data item or a combination of data items to which there is assigned a trigger. The trigger definition table is user definable. In each trigger record of trigger definition table 412, there is a type and a code entry for each data item which establishes a triggering event. For example, a data type may be a generic class of the prescribed drug and the code is the generic class code, labelled a "link" in FIG. 4, for that drug. A second data item could be the patient's age. These data items will not necessarily be entered in the prescription record table for the particular transaction. However, the trigger record building or creation process will associate the data items recorded in the prescription table with the data items defined in the trigger table, as represented by the lines 416 drawn between the illustrated table record structures in FIG. 4.

If a match is found, as indicated by step 316, a patient care action record for the particular transaction is created in step 318. If no match is found, then the routine proceeds to step 326 to determine whether the prescription can be completed. Step 318 involves looking up all patient care actions specified in the record of the matched trigger(s) in an action definition table 414. This looking up is represented by line 418, in which the action identifier in the trigger table is found in the care action table. Multiple actions may be specified. The details of the actions listed in the patient care action record are then automatically displayed in a queue to the pharmacist at step 320. The structure of the action action definition table includes a table ID and level code. Multiple action tables may be maintained for use by other processes, such as those in the care management system 106 (FIG. 1). Additionally, a description is provided for display. A predefined action type and instruction are entered for initiating the appropriate processes in the care management system 106. Finally, a fee and note can also included for each action.

At step 322, the pharmacist is given the option of initiating the patient care action(s), skipping them, or holding them for later initiation. If one or more of the care actions are initiated, appropriate processes in the pharmacy care services system 106 are automatically loaded and executed at step 324 in sequence for handling the initiated care actions. After the processes are loaded and executed, the process continues to step 326. Also, if the pharmacist chooses not to initiate the actions, the process continues to step 326.

At step 326, if the prescription cannot be completed because, for example, a severe drug conflict is found, then the prescription process is stopped. However, if the prescription process is able to proceed, then a new entry for the transaction is written to the prescription record table 402 at this point. At step 328, the trigger record is once again matched to the trigger table to determine whether there are any matches for records which are to be performed only after the prescription record is written. An indication of whether the action is for initiation before or after step 326 is included in the action definition table. If a match is found, as indicated by decision step 330, an action record is created and the actions are displayed, initiated and executed in steps 332, 334, 336 and 338 in the same manner as steps 318, 320, 322 and 324, respectively.

If no actions are initiated, if no match is found at step 330, or upon completion of the execution of the last action by the care service system 106, the practice management system 102 may submit a claim by modem if desired, as indicated by steps 340 and 342. The final step 344 is printing labels for the drug packaging. Labels are printed whether the claim is submitted by modem, through step 342, or not, as shown after step 340.

Generally, any number of data elements can serve as triggers. Examples of possible triggers include: patient name, age, disease state, payment plan; doctor name; drug NDC, generic class, therapeutic class and manufacturer; refill date, instructions and ICD-9 code; and DUR conflict. Possible patient care actions that could be performed by pharmacy care management system 106 include the following. An appointment can be scheduled for monitoring a condition such as tests for blood pressure, breathing (asthma) and blood glucose levels (diabetes). A predefined batch process can be automatically run on the computer. The pharmacist can issue a coupon for a drug or other item in the pharmacy based on, for example, the disease state of the patient. Patient drug information can be printed as well as claim forms. An intervention can be recorded or an S.O.A.P. protocol performed in connection with, for example, patient counselling in the pharmaceutical care process or disease management process. A note can be entered, edited or displayed. Another program can be called. A rebate can be applied to the price of the drug. A claim can be submitted to an insurance company. Standard supplemental instructions, such as from a doctor, could be printed for the patient. A questionnaire can be initiated with which to collect lifestyle information, or a lifestyle management process initiated.

Figure 5A:
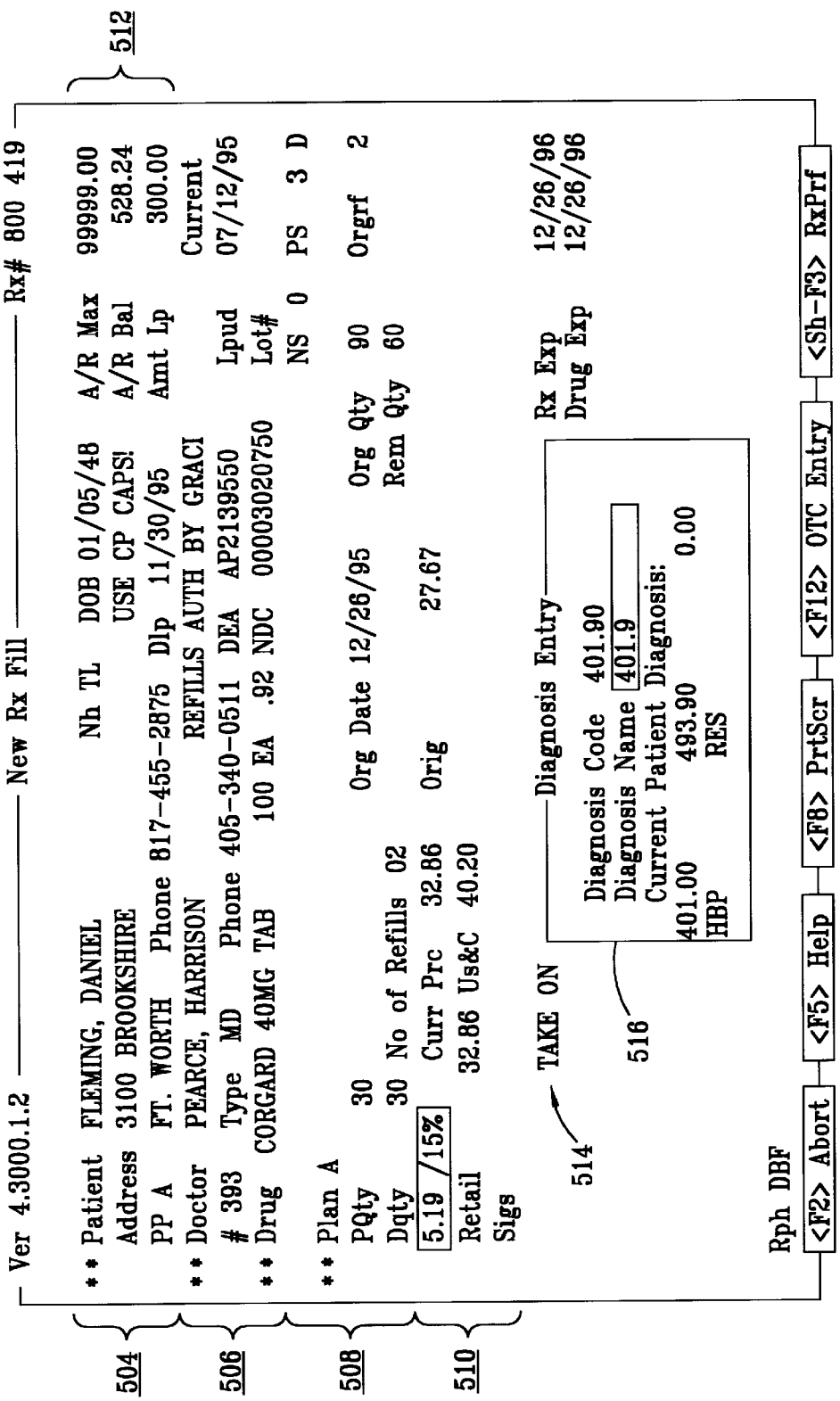

Referring to FIG. 5a, as already described, a prescription record having the structure 402 is created and kept in the database file(s) for the practice management system 102 each time a drug is dispensed. An example of the screen which creates this record is the new refill prescription screen 502. The pharmacists enters certain information. The program will then look up additional details concerning the patient, drug, billing and doctor from database records such as those whose structures are shown in FIG. 4, for example the patient records 402, doctor records, drug records 404, and billing records and display this information. In screen 502, patient information is displayed in the area indicated by bracket 504, doctor information is displayed in the area indicated by bracket 506, drug information is displayed in the area indicated by bracket 508, drug pricing information is in the area indicated by bracket 510, and billing information is indicated in the area indicated by bracket 512. Instructions are entered in the area designated 514. Some of these records can be edited or new entries made through a window in the screen. For example, diagnosis entry window 516 enables the pharmacist to edit or enter additional patient diagnosis codes stored in the patient records 404 (FIG. 4). In this example, the patient disease code corresponding to high blood pressure has been assigned to the patient.

Referring to FIG. 5b, patient care action edit screen 520 is overlaid on the prescription refill screen 502 at steps 320 and 334 in FIGS. 3a and 3b by the triggering or linking system 104. This patient care action screen includes patient information displayed in area 522 taken from the patient files maintained by the practice management system 102. It lists in area 523 the title or descriptions of the actions in the action record created in steps 318 and 332, as well as the fee charged by the pharmacy for those actions. These actions were triggered by the presence in this patient's record of a disease code for high blood pressure. The two actions are scheduling a weekly monitoring of blood pressure and printing a hypertension diet instruction sheet. Menu window 524 lists options from which the pharmacist may select from this screen: initiate all actions with a "y" or yes status, which is shown in column 523, change the status of one or more of the actions, print the list or exit the screen.

Referring now to FIG. 5c, if the pharmacist selects the change status option, menu window 526 display the possible code options. "Y" indicates that the action be initiated when instructed. "I" means initiate the action immediately. "N" causes the action to skipped. And "D" closes the action. The screens of FIGS 5b and 5ccorrespond to steps 322 and 336 of FIGS. 3a and 3b. Referring now to FIG. 5d, if the initiate all option is selected from menu window 524 in FIG. 5b, the triggering or linking system 104 initiates the process specified by the first listed action, namely the patient scheduling process. Appointment information is entered through patient scheduling screen 528. The patient information in the area indicated by bracket 530 is retrieved from the patient information records kept by the practice management system 102. Data, time and frequency are entered. Additionally, as indicated by bracket 532, up to five monitoring procedures may be entered on the screen to be performed by the indicated technician during each appointment. The blood pressure procedure is automatically entered by the program since that monitoring procedure was defined in the patient care action.

Figure 6A:
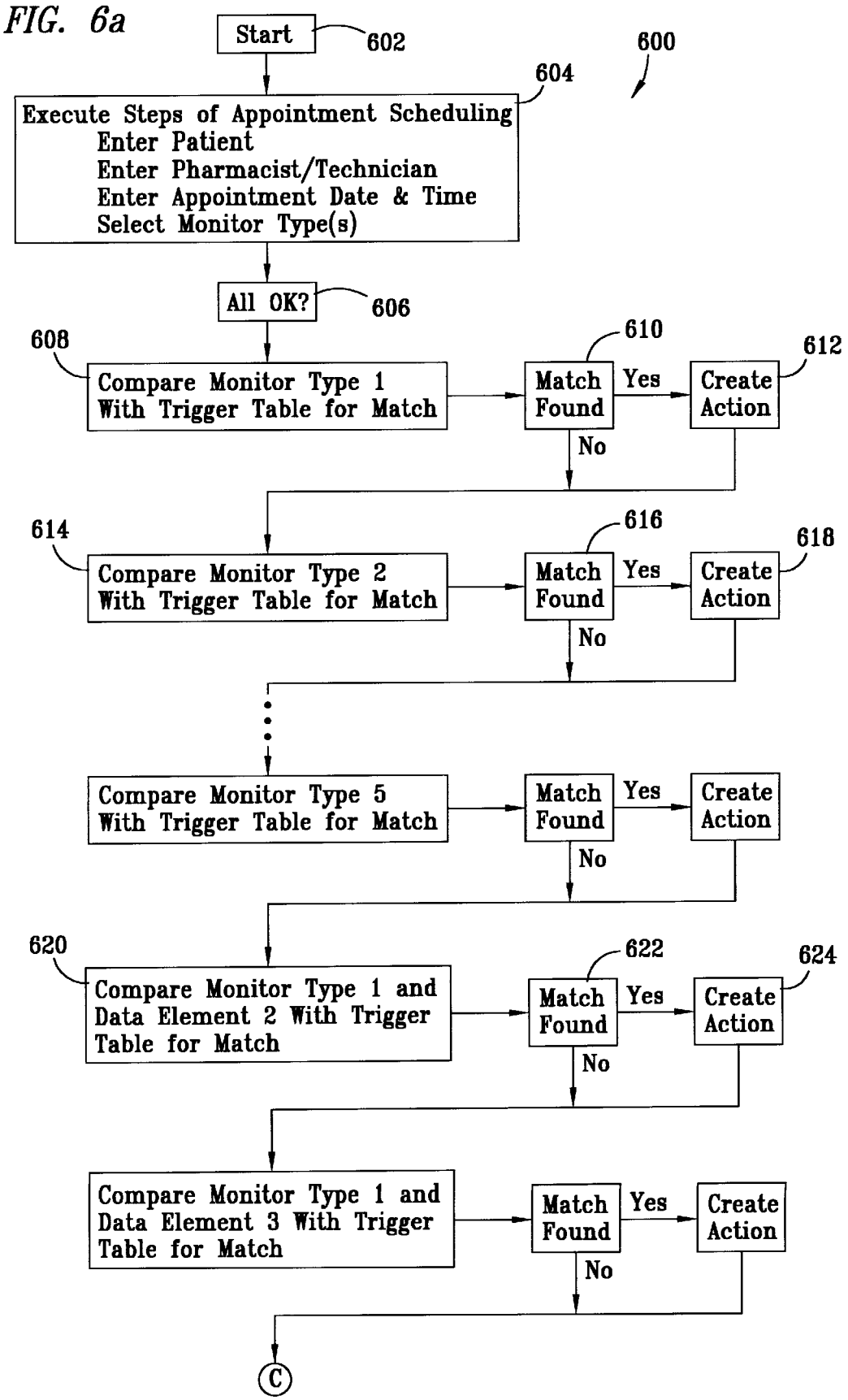
FIGS. 6A–6C is a flow diagram illustrating a representative process of a pharmacy care management system for scheduling appointments for monitoring patients and linking other patient care actions to the appointment scheduling for automatic execution.
Figure 6B:
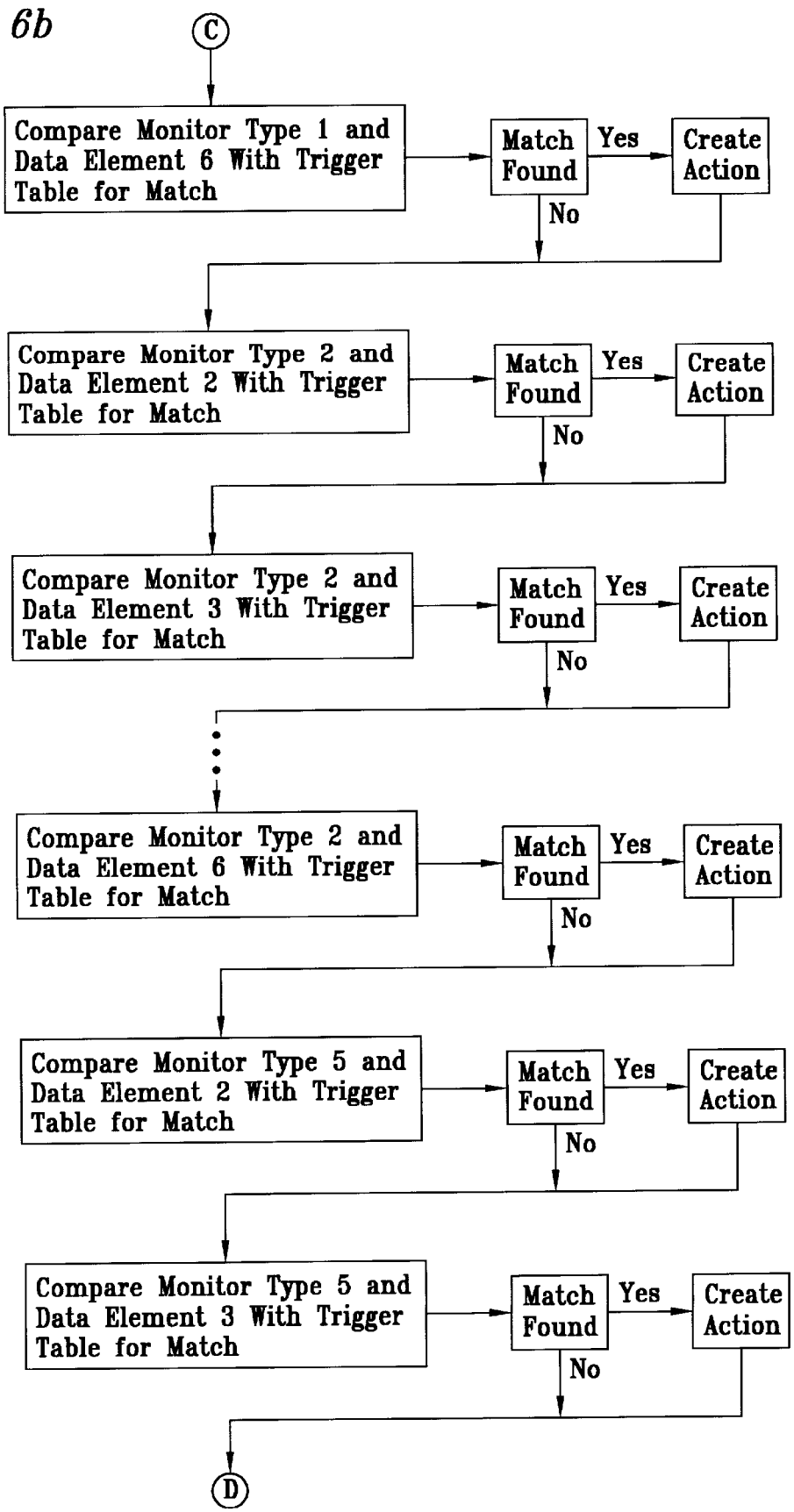
Figure 6C:
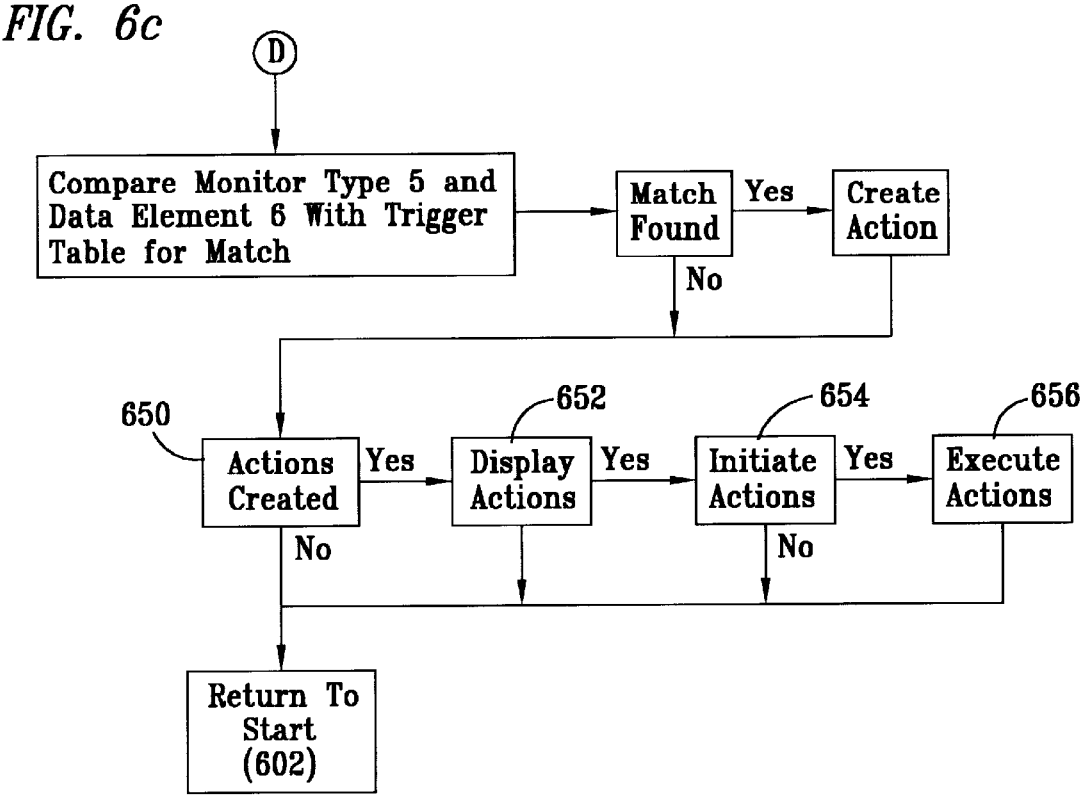

Now referring to FIGS. 6a through 6c, there is illustrated a process 600 for scheduling an appointment or initiating the execution of actions for the monitoring of one or more health aspects of a patient. Further, the process includes searching a trigger table and selecting an/or creating an action based on certain criteria (i.e the type of monitoring to be performed and/or data or other information about the patient (such as name, age, disease state, lifestyle condition) or other criteria (date, monitoring event).

Now referring to FIG. 6a, the process 600 begins at a starting point 602. The process 600 is one of the core set of complementary care processes 108 which is either triggered by execution of a process in the pharmacy practice management system 102 or started by the user in pharmacist care service system 106. At a step 604, an appointment is scheduled or recorded by inputing information regarding the patient and the appointment, such as patient name, the pharmacist or technician to perform the monitoring test(s), appointment date and time, and the type of monitoring to be performed on the patient. As will be appreciated, numerous monitor types may be entered depending on the desired health service(s) of the patient to be monitored. Examples of some monitoring actions that may be scheduled include monitoring blood-sugar level, blood pressure and pulse rate, flow metering (for asthma sufferers), etc. and may include any other types of health monitoring as desired. After the appointment data is entered at the step 604, the user verifies that the entered appointment data is correct and in the proper format at a step 606 before proceeding to the next steps.

After the step 606 is completed, a predefined trigger table stored as part of an informational database is searched according to the monitor type set forth in the scheduled appointment and/or according to the monitor type in conjunction with other data. In a step 608, monitor type 1 entered in the step 604 is compared to a trigger table (not shown) for a match. At a step 610, it is determined if a match is found. If a match between the monitor type and the trigger table is found, an action is identified and placed in the action queue at a step 612. As will be appreciated, the action created may include actions such as to schedule another appointment, initiate a batch process, issue a coupon, print a claim form, enter, edit, display or print a note, call another program, submit a claim, initiate lifestyle management, record or initiate monitoring, S.O.A.P., printout supplemental data, key-in data, etc. As will be appreciated, one or more actions may be created for a given match with the entered monitor type. As an example, if a match occurred for the monitor type, one of the actions created may be to display to the user an action for printing out an appointment card for the patient listing (1) the name of the patient, (2) the type of monitoring action to be performed, (3) the location, date and time of the appointment and (4) any other information as deemed necessary or desired.

If no match was found in step 610, or after creating the specified action at the step 612, the process continues to a step 614. In the step 614, the monitor type (if the monitor type is equal to Monitor Type 2) entered in the step 604 is compared to a trigger table (not shown) for a match. At a step 616, it is determined if a match is found. If a match between the monitor type and the trigger table is found, an action is identified and placed in the action queue at a step 618. It will be understood, that the process continues searching the trigger table for all the monitor types that are entered in the step 604. In FIG. 6a, the process 600 is shown searching for one or more of five possible monitor types in a series of steps to match the monitor types entered in step 604 (one or more may be entered, if the patient has, or desires an appointment for monitoring of more than one health aspect) with any corresponding actions set forth in the trigger table. As will be appreciated, the number of possible monitor types may be any number depending on the number desired.

After identifying and queuing actions corresponding solely to the entered monitor type, the trigger table is again searched to determine if any actions exist that correspond to a particular given monitor type cross-indexed with other information about the patient (such as name, age, disease state, lifestyle condition)) or other criteria (date, monitoring event). This other information or other criteria are referred to as data elements. The data elements have been previously entered into the database (i.e. patient name, age disease state, information on lifestyle, dates and monitoring events) or can be entered by the user at anytime. For example, an action or actions may be created according to the monitor type and the patient's age.

In a step 620, the monitor type (if the monitor type is equal to Monitor Type 1) entered in the step 604 and the data element 2 (i.e. the patient's age meets some predetermined threshold) is compared to a trigger table (not shown) for a match. As such, an action is identified and created from the trigger table and placed in the queue if an action exists when the monitor type is monitor type 1 and the patient's age is, for example, greater than 65. At a step 622, it is determined if a match is found. If a match between the monitor type in conjunction with the data element 2 and the trigger table is found, an action is identified and placed in the queue at a step 624. Again, the action created could be any of the actions as described above or others. If no match was found in step 622, or after creating the specified action at the step 624, the process 600 continues to search the trigger table for actions corresponding to the monitor type 1 in conjunction with data element 3, the monitor type 1 in conjunction with data element 4, and so on, as shown in FIGS. 6a and 6b. In addition, the process 600 searches the trigger table for actions corresponding to the monitor type 1 and data elements 1 through 6, the monitor type 3 and data elements 1 through 6, and so on, as shown in FIGS. 6b and 6c.

After all monitor types are searched (with and without data element criteria), it is determined at a step 650 whether any actions were identified and placed in a queue. If not, the process returns to the start so that other actions may be performed by the user. If one or more actions are created, the actions are displayed to the user at a step 652. Further, the actions may be initiated by the user at a step 654 and executed at a step 656. If the user chooses not to initiate the action actions at step 654, the process returns to start.

Now referring to FIGS. 7a and 7b, there are illustrated examples of a screen output (displays) associated with the process 600. Now referring to FIG. 7a, there is illustrated a typical patient appointment data screen. The screen is generally displayed on request by the user when a patient arrives for a monitoring procedure or when a patient needs to be scheduled for an appointment. As shown in FIG. 7a, the screen contains patient information, the name of the pharmacist/technician, appointment time and date, next appointment time and date, and monitor type (monitoring procedure) shown as BP (blood pressure monitoring). After the user verifies that all the entered information is correct, the process 600 searches the trigger table according to the above described process and any actions that are created will be identified to the user.

Now referring to FIG. 7b, there are shown examples of displayed actions created by the process 600. As shown, three actions were created: (1) hand out worksheet #1, (2) schedule next appointment and (3) check and record blood pressure and pulse. Once displayed, the actions can be initiated by the user, i.e. step 654. If initiated, the user can then execute, i.e. step 656, the specific action initiated. As will be appreciated, the process 600 of the present invention may be used alone as a complementary care service and/or used in conjunction with other complementary care services or the management system 102.

Although the present invention and its advantages have been described in the foregoing detailed description and illustrated in the accompanying drawings, it will be understood by those skilled in the art that the invention is not limited to the embodiment(s) disclosed but is capable of numerous rearrangements, substitutions and modifications without departing from the spirit and scope of the invention as defined by the appended claims.

What is claimed is:

1. A data processing method for managing delivery of healthcare services comprising the steps of:

executing a first process in a specially programmed data processing system having an electronic memory for recording a plurality of predefined data items obtained from an outside source, the data items associated with dispensing pharmaceutical drugs in a prescription-based transaction;

determining whether a trigger stored in the electronic memory of the data processing system is associated with the plurality of data items in response to using the prescription-based transaction; and executing a second data process for use in connection with providing a healthcare-related action that improves an effectiveness of a drug therapy, the healthcare-related action identified by the trigger.

2. The data processing method of claim 1 where in the step of executing a second data process further comprises the steps of:

queuing the healthcare-related action identified by the trigger in response to an input of the user to the prompt;

providing selection by a user of the healthcare-related action for execution by the second data process; and engaging the healthcare-related action in response to the selection of the healthcare-related action by the user.

3. The data processing method of claim 1 wherein the healthcare-related action includes monitoring a condition of the patient with a healthcare giver.

4. The data processing method of claim 1 wherein the outside source is a database.

5. The data processing method of claim 1 wherein the outside source is a user entering in the data items into the data processing system.

6. The data processing method of claim 1 wherein the first process comprises a pharmacy practice management system for dispensing pharmaceutical drugs in a prescription-based transaction.

7. The data processing method of claim 1 wherein the healthcare-related action comprises a care management system.

8. A data processing method for managing delivery of healthcare services comprising the steps of:

executing a first process in a specially programmed data processing system having an electronic memory for recording a plurality of predefined data items obtained from an outside source, the data items associated with dispensing pharmaceutical drugs in a prescription-based transaction;

determining whether a trigger stored in the electronic memory of the data processing system is associated with the plurality of data items in response to using the prescription-based transaction; and executing a second data process for use in connection with providing a healthcare-related action that improves an effectiveness of a drug therapy, the healthcare-related action identified by the trigger, and the second data process prompting a user to engage the healthcare-related action.

9. The data processing method of claim 8 wherein the step of executing a second data process further comprises the steps of:

queuing the healthcare-related action identified by the trigger in response to an input of the user to the prompt; and engaging the healthcare-related action identified by the trigger in response to the selection by the user of the healthcare-related action identified by the trigger.

10. The data processing method of claim 8 wherein the healthcare-related action includes monitoring a condition of the patient.

11. The data processing method of claim 8 wherein the outside source is a database.

12. The data processing method of claim 8 wherein the outside source is a user entering in the data items into the data processing system.

13. The data processing method of claim 8 wherein the first process comprises a pharmacy practice management system for dispensing pharmaceutical drugs in a prescription-based transaction.

14. The data processing method of claim 8 wherein the healthcare-related action comprises a care management system.

15. A computer system for managing delivery of healthcare services comprising:

means for recording a plurality of predefined data items from an outside source, said plurality of predefined data items associated with dispensing pharmaceutical drugs in a prescription-based transaction;

means for determining whether a trigger stored in the computer system is associated with said plurality of predefined data items in response to using said prescription-based transaction; and means for responding to said trigger with a healthcare-related action that improves an effectiveness of a drug therapy.

16. The computer system of claim 15 wherein said healthcare-related action displays a prompt for a user to engage said healthcare-related action, said prompt for requiring a response from said user.

17. A method for improving the effectiveness of a drug therapy, the method comprising the steps of:

providing a pharmacy practice management system executable on a computer, the pharmacy practice management system having at least one set of predefined data items associated with a patient, the at least one set of predefined data items being associated with dispensing pharmaceutical drugs in a prescription-based transaction;

triggering a care service process with respect to an interaction of a prescription with the at least one set of predefined data items associated with the patient, the care service process providing an increased effectiveness of the prescription in treating the patient; and administering the care service process on behalf of the patient.

18. The method for improving the effectiveness of a drug therapy of claim 17, wherein the care service process is a process of intervention on behalf of the patient.

19. The method for improving the effectiveness of a drug therapy of claim 17, wherein the set of predefined data items includes at least one medical history data item.

20. Apparatus for improving the effectiveness of a drug therapy comprising:

a computer system having a pharmacy practice management system executable on said computer system, said pharmacy practice management system having at least one set of predefined data items associated with a patient, said at least one set of predefined data items being associated with dispensing pharmaceutical drugs in a prescription-based transaction; and a care service process linked with said pharmacy practice management system and executable on said computer system, said care service process triggered in response to an interaction of a prescription with said at least one set of predefined data items associated with the patient, said care service process providing an increased effectiveness of the prescription in treating the patient by providing an additional treatment complementary to said prescription.

* * * * *